United States Patent [19]

Brisken

[11] Patent Number: 5,725,494
[45] Date of Patent: Mar. 10, 1998

[54] APPARATUS AND METHODS FOR ULTRASONICALLY ENHANCED INTRALUMINAL THERAPY

[75] Inventor: Axel F. Brisken, Fremont, Calif.

[73] Assignee: Pharmasonics, Inc., Mountain View, Calif.

[21] Appl. No.: 565,575

[22] Filed: Nov. 30, 1995

[51] Int. Cl.$^6$ .................................................. A61B 17/20
[52] U.S. Cl. .................................................. 604/22; 606/169
[58] Field of Search .......................... 606/169; 607/97; 604/22; 601/2; 310/26

[56] References Cited

U.S. PATENT DOCUMENTS

| | | | |
|---|---|---|---|
| 3,433,226 | 3/1969 | Boyd | 128/305 |
| 3,565,062 | 2/1971 | Kuris | 128/24 |
| 4,636,195 | 1/1987 | Wolinsky | 604/53 |
| 4,692,139 | 9/1987 | Stiles | 604/22 |
| 4,698,058 | 10/1987 | Greenfeld et al. | 604/266 |
| 4,808,153 | 2/1989 | Parisi | 604/22 |
| 4,838,853 | 6/1989 | Parisi | . |
| 4,870,953 | 10/1989 | DonMichael et al. | 128/24 |
| 4,936,281 | 6/1990 | Stasz | 128/660.03 |
| 4,948,587 | 8/1990 | Kost et al. | 424/435 |
| 5,085,662 | 2/1992 | Willard | 606/159 |
| 5,163,421 | 11/1992 | Berstein et al. | 128/24.1 |
| 5,197,946 | 3/1993 | Tachibana | 604/22 |
| 5,267,954 | 12/1993 | Nita | 604/22 |
| 5,267,985 | 12/1993 | Shimada et al. | 604/290 |
| 5,269,291 | 12/1993 | Carter | 128/24 |
| 5,269,297 | 12/1993 | Weng et al. | 128/24 |
| 5,279,546 | 1/1994 | Mische et al. | 604/22 |
| 5,282,785 | 2/1994 | Shapland et al. | 604/21 |
| 5,286,254 | 2/1994 | Shapland et al. | 604/21 |
| 5,304,115 | 4/1994 | Pflueger et al. | 604/22 |
| 5,315,998 | 5/1994 | Tachibana et al. | 128/660 |
| 5,318,014 | 6/1994 | Carter | 601/2 |
| 5,324,255 | 6/1994 | Passafaro et al. | 604/22 |

(List continued on next page.)

FOREIGN PATENT DOCUMENTS

| | | | |
|---|---|---|---|
| 0 189 329 | 7/1986 | European Pat. Off. | A61B 17/22 |
| 3-063041 | 3/1991 | Japan | A61B 17/22 |
| WO 90/01300 | 2/1990 | WIPO | A61B 17/32 |
| WO 91/19529 | 12/1991 | WIPO | A61M 29/02 |
| WO 94/05361 | 3/1994 | WIPO | A61M 25/00 |
| WO 95/22284 | 8/1995 | WIPO | A61B 8/12 |
| WO 95/24159 | 9/1995 | WIPO | A61B 17/36 |

OTHER PUBLICATIONS

Rosenschein, U. et al. "Experimental Ultrasonic Angioplasty: disruption of Atherosclerotic Plaques and Thrombi in Vitro and Arterial Recanalization in Vivo." (1990) JACC vol. 15, No. 3, pp. 711–717.

Yumita, N. et al. "Synergistic Effect of Ultrasound and Hematoporphyrin on Sarcoma 180." (1990) JPN. J. CANCER RES. 81, pp. 304–308.

Tachibana, K. "Enhancement of Fibrinolysis with Ultrasound Energy." (1992) J. Vascular & Interventional Radiography 3(2) pp. 299–303.

*Primary Examiner*—Mark Bockelman
*Attorney, Agent, or Firm*—Townsend and Townsend and Crew LLP

[57] ABSTRACT

An ultrasonic catheter comprises a catheter body having a resonantly vibrating assembly at its distal end. The resonantly vibrating assembly comprises a tail mass, an interface member, and a spring element which connects the tail mass to the interface member. An interface surface is formed on the interface member and is forwardly disposed at the distal end of the catheter. A longitudinally oscillating driver is disposed between the tail mass and the interface member, and the catheter can be connected to a suitable power supply to induce oscillations in the driver. The driver is typically a piezoelectric device, such as a tubular piezoelectric transducer or a piezoelectric stack. The characteristics of the interface member, spring element, and longitudinally oscillating driver are selected so that the interface member may be resonantly vibrated at an ultrasonic frequency. The catheter is useful for treating luminal conditions, such as vascular clot and plaque. Optionally, a therapeutic agent may be delivered through the catheter simultaneously with the application of ultrasonic energy.

37 Claims, 5 Drawing Sheets

U.S. PATENT DOCUMENTS

| | | | |
|---|---|---|---|
| 5,342,292 | 8/1994 | Nita et al. | 604/22 |
| 5,344,395 | 9/1994 | Whalen et al. | 604/22 |
| 5,362,309 | 11/1994 | Carter | 604/22 |
| 5,380,273 | 1/1995 | Dubrul et al. | 604/22 |
| 5,397,301 | 3/1995 | Pflueger et al. | 604/22 |
| 5,447,509 | 9/1995 | Mills et al. | 606/1 |
| 5,456,259 | 10/1995 | Barlow et al. | 128/662.03 |
| 5,458,568 | 10/1995 | Racchini et al. | 604/19 |
| 5,458,631 | 10/1995 | Xavier | 607/117 |
| 5,462,523 | 10/1995 | Samson et al. | 604/30 |
| 5,465,725 | 11/1995 | Seyed-Bolorforosh | 128/662.03 |
| 5,474,530 | 12/1995 | Passafaro et al. | 604/22 |
| 5,474,531 | 12/1995 | Carter | 604/22 |

APPARATUS AND METHODS FOR ULTRASONICALLY ENHANCED INTRALUMINAL THERAPY

BACKGROUND OF THE INVENTION

1. Field of the Invention

The present invention relates generally to medical devices and methods. More particularly, the present invention relates to apparatus and methods for the localized delivery of therapeutic ultrasound energy within the vasculature and other body lumens.

Despite the growing sophistication of medical technology, vascular (blood vessel) diseases, such as acute myocardial infarction (heart attack) and peripheral arterial thrombosis (blood clots in leg arteries), remain a frequent, costly, and very serious problem in health care. Current methods of treatment, often expensive, are not always effective. In the U.S. alone, the cost of treatment and support and the loss of productivity due to vascular diseases together exceed $40 billion per year.

The core of the problem is that diseased sites within the blood vessels narrow and eventually become completely blocked as a result of the deposition of fatty materials, cellular debris, calcium, and/or blood clots, thereby blocking the vital flow of blood. Current treatments include drugs, interventional devices, and/or bypass surgery. High doses of thrombolytics (clot-dissolving drugs) are frequently used in an effort to dissolve the blood clots. Even with such aggressive therapy, thrombolytics fail to restore blood flow in the affected vessel in about 30% of patients. In addition, these drugs can also dissolve beneficial clots or injure healthy tissue causing potentially fatal bleeding complications.

While a variety of interventional devices are available, including angioplasty, atherectomy, and laser ablation catheters, the use of such devices to remove obstructing deposits may leave behind a wound that heals by forming a scar. The scar itself may eventually become a serious obstruction in the blood vessel (a process known as restenosis). Also, diseased blood vessels being treated with interventional devices sometimes develop vasoconstriction (elastic recoil), a process by which spasms or abrupt reclosures of the vessel occur, thereby restricting the flow of blood and necessitating further intervention. Approximately 40% of treated patients require additional treatment for restenosis resulting from scar formation occurring over a relatively long period, typically 4 to 12 months, while approximately 1-in-20 patients require treatment for vasoconstriction, which typically occurs from 4 to 72 hours after the initial treatment.

Bypass surgery can redirect blood around the obstructed artery resulting in improved blood flow. However, the resulting bypass grafts can themselves develop scar tissue and new blood clots in five to ten years resulting in blockage and the need for further treatment. In summary, all current therapies have limited long term success.

The use of ultrasonic energy has been proposed both to mechanically disrupt clot and to enhance the intravascular delivery of drugs to dissolve clot and inhibit restenosis. Ultrasonic energy may be delivered intravascularly using specialized catheters having an ultrasonically vibrating surface at or near their distal ends. One type of ultrasonic catheter employs a wire or other axial transmission element to deliver energy from an ultrasonic energy vibration source located outside the patient, through the catheter, and to the ultrasonically vibrating surface. While such systems can deliver relatively large amounts of energy, the need to transmit that energy through the entire length of the catheter presents a substantial risk to the patient.

Moreover, such catheters are typically rigid and cannot easily traverse narrow, tortuous arteries, such as the coronary arteries which frequently need to be treated. Because of their rigidity and inability to follow the vascular lumen, these catheters present a serious risk of vascular wall perforation.

In order to avoid the use of ultrasonic transmission members, catheters having ultrasonic transducers mounted directly on their distal ends have also been proposed. See, for example, U.S. Pat. Nos. 5,362,309; 5,318,014; 5,315,998; 5,269,291; and 5,197,946. By providing the transducer within the catheter itself, there is no need to employ a transmission element along the entire length of the catheter. While such catheter designs offer enhanced safety, they suffer from a limited ability to generate large amounts of ultrasonic energy. Even though certain of these designs, such as that described in U.S. Pat. No. 5,362,309, employ "amplifiers" which enhance the delivery of ultrasonic energy, such designs are still problematic. In particular, the catheters of the '309 patent have relatively long, rigid transducers and are not amenable to receiving guidewires, both of which features make it difficult to position the catheters within the vasculature, particularly the coronary vasculature.

For these reasons, it would be desirable to provide improved ultrasonic catheter designs overcoming at least some of the problems discussed above. In particular, it would be desirable to provide ultrasonic catheters having ultrasonic transducers at their distal ends, where the transducers are capable of driving interface surfaces with relatively high energy and amplitude. It would further be desirable to provide transducer and driver designs which are highly efficient and which minimize the production of heat within the vascular or other luminal environment. It would be still further desirable to provide methods for the intraluminal delivery of ultrasonic energy, where the ultrasonic energy is useful for a variety of purposes, including the direct mechanical disruption of clot, the enhancement of thrombolytic activity of agents to dissolve clot, and the enhancement of pharmacologic agents to prevent restenosis of vascular sites previously treated by angioplasty or other interventional methods.

2. Description of the Background Art

Catheters having ultrasonic elements with the capability of delivering thrombolytic and other liquid agents are described in U.S. Pat. Nos. 5,362,309; 5,318,014; 5,315,998; 5,197,946; 5,397,301; 5,380,273; 5,344,395; 5,342,292; 5,324,255; 5,304,115; 5,279,546; 5,269,297; 5,267,954; 4,870,953; 4,808,153; 4,692,139; and 3,565,062; in WO 90/01300; and in Tachibana (1992) JVIR 3:299–303. A rigid ultrasonic probe intended for treating vascular plaque and having fluid delivery means is described in U.S. Pat. No. 3,433,226. An ultrasonic transmission wire intended for intravascular treatment is described in U.S. Pat. No. 5,163,421 and Rosenschein et al. (1990) JACC 15:711–717. Ultrasonically assisted atherectomy catheters are described in U.S. Pat. No. 5,085,662 and EP 189329. Ultrasonic enhancement of systemic and localized drug delivery is described in U.S. Pat. Nos. 5,286,254; 5,282,785; 5,267,985; and 4,948,587; in WO 94/05361 and WO 91/19529; in JP 3-63041; and Yumita et al. (1990) JPN. J. CANCER RES. 81:304–308. An electrosurgical angioplasty catheter having ultrasonic enhancement is described in U.S. Pat. No. 4,936,281. An infusion and drainage catheter having an ultrasonic cleaning mechanism is described in U.S. Pat. No. 4,698,058. A drug delivery catheter having a pair of spaced-apart balloons to produce an isolated region around arterial plaque is described in U.S. Pat. No. 4,636,195.

SUMMARY OF THE INVENTION

According to the present invention, a catheter for the intraluminal delivery of ultrasonic energy comprises a catheter body having a proximal end and a distal end. A tail mass is attached to the catheter body, typically at its distal end, and a longitudinally oscillating driver engages and extends distally from the tail mass. An interface member is disposed to engage a distally forward surface of the oscillating driver, and the mass of the interface member is much less than that of the tail mass. The tail mass and interface member are connected to each other by a spring element so that a resonant system is formed for driving the interface member. By employing a relatively large tail mass, the resonant frequency of the interface member, spring element, and oscillating driver is independent of the tail mass and defined primarily by the mass of the interface member and the elastic modulus of the spring element, and the oscillating driver. By properly choosing the operating frequency of the longitudinally oscillating driver, the resonant system defined by the interface member, the spring element, and the oscillating driver can be resonantly driven to enhance both the displacement amplitude of an interface surface on the interface member and increase the efficiency of operation, i.e., the conversion of electrical energy to mechanical energy.

The longitudinally oscillating member may take any conventional form for an ultrasonic transducer, typically being a tubular piezoelectric transducer, a piezoelectric stack, or the like. An exemplary tubular piezoelectric transducer comprises a hollow piezoelectric cylinder having an inner cylindrical electrode and an outer cylindrical electrode. Application of a driving current to the electrodes causes axial and radial expansion and contraction of the piezoelectric transducer. The axial expansion and contraction allow the piezoelectric cylinder to resonantly drive the interface member in the longitudinal direction. An exemplary piezoelectric stack comprises a plurality of ceramic disks having electrodes therebetween.

The spring element will comprise an axial member capable of mechanically coupling the interface member to the tail mass with sufficient space therebetween to receive the longitudinal driver. Typically, the spring element will comprise at least one rod secured at a proximal end to the tail mass and at a distal end to the interface member. The rod may optionally be tubular to provide the path for a guidewire, infusion of therapeutic agent, or the like. A single rod will usually be disposed coaxially within the catheter. Multiple rods may be disposed symmetrically about the axis of the catheter body. Alternatively, the spring element may comprise a thin-walled cylindrical member secured to the tail mass and the interface member and enclosing the longitudinally oscillating member in a concentric manner.

The interface member will usually include a distally disposed interface surface which forwardly transmits longitudinal oscillations into the environment surrounding the distal end of the catheter. The interface surface will typically be convex, although it could be flat, concave, or irregular.

A method according to the present invention for treating intraluminal lesions comprises providing a catheter having an interface member at its distal end. A forwardly disposed surface of the interface member is advanced to a region near the intraluminal lesion, typically to a region of vascular stenosis within a patient's vasculature, and the interface member is resonantly driven relative to a tail mass mounted proximally of the interface member. In this way, ultrasonic energy is efficiently delivered into the regions surrounding the distal end of the catheter. The interface member is typically driven at a frequency in the range from 10 kHz to 300 kHz, and will have a longitudinal amplitude in the range from about 0.05 μm to 20 μm, under typical mass loading conditions of a vascular lumen. The forwardly disposed surface of the interface member will typically have an area in the range from 0.5 mm$^2$ to 20 mm$^2$, and the catheter may be used in a variety of specific therapeutic protocols.

In a first such protocol, the interface member will be engaged directly against a vascular obstruction and used to ablate the structure or optionally to dissolve the structure with the simultaneous delivery of a thrombolytic or fibrinolytic agent. Alternatively, the catheter can be used to deliver ultrasonic energy into an environment where a thrombolytic or fibrinolytic agent has been delivered, where the catheter need not be directly engaged against clot or other stenoses. In such cases, the ultrasonic energy will enhance the activity of the therapeutic agent, typically by improving penetration of the agent into the clot. In a third exemplary protocol, the catheter may be used to deliver an anti-thrombotic agent to a previously treated vascular site to inhibit restenosis. Again, the ultrasonic energy will typically provide for enhanced delivery and penetration of the anti-thrombotic agent into the blood vessel wall. In a fourth exemplary protocol, the catheter may be used to dissolve the clot, without the adjunct benefit of thrombolytic agents.

DESCRIPTION OF THE SPECIFIC EMBODIMENTS

Figure 1:
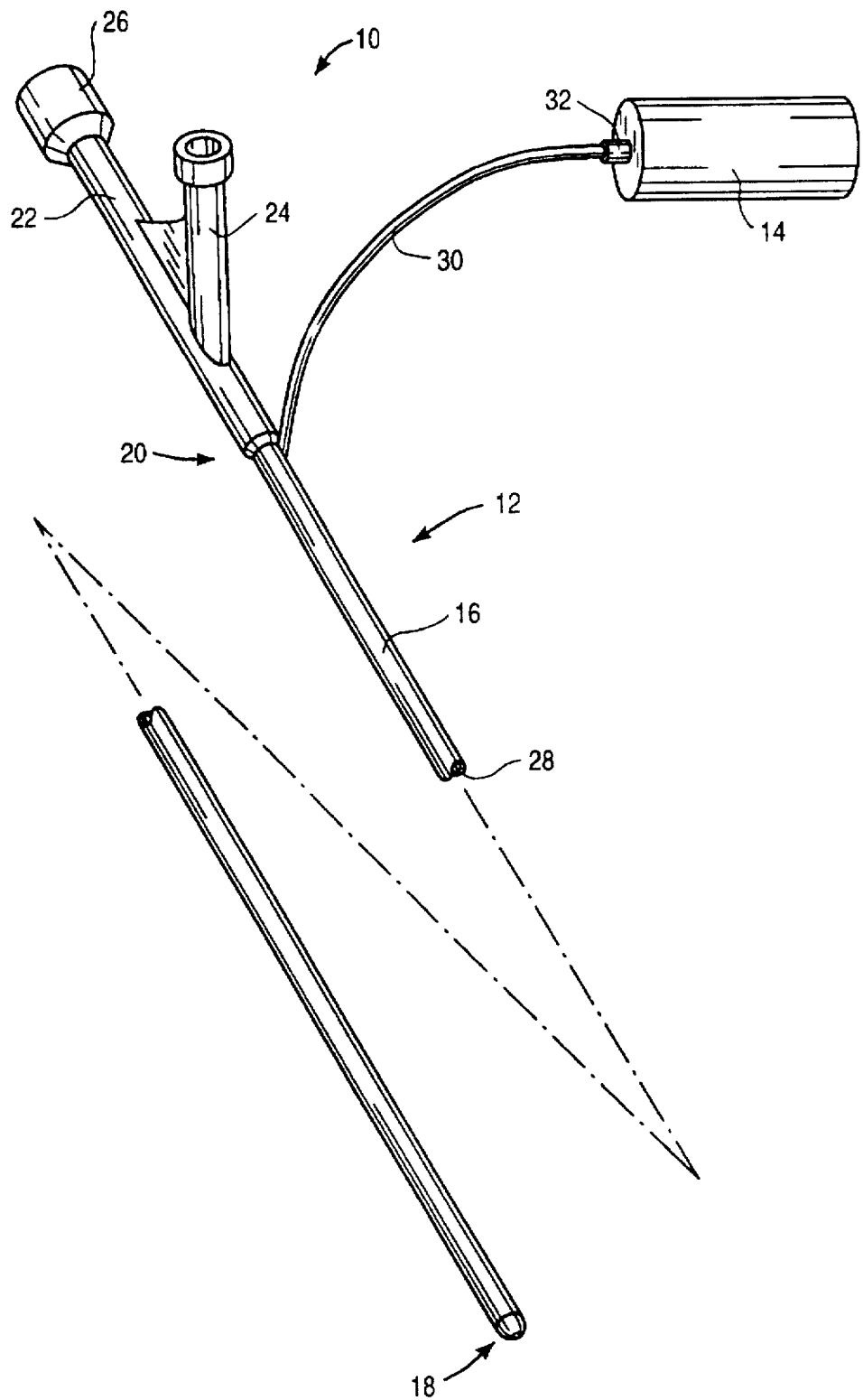
FIG. 1 illustrates an exemplary catheter and ultrasonic energy source constructed in accordance with the principles of the present invention.

The present invention provides apparatus and methods for the treatment of luminal conditions, particularly for the treatment of diseases of the coronary and peripheral vasculature. Specific conditions include coronary and peripheral arterial disease and thrombosis. The apparatus and methods are useful for primary treatment of such diseases, where the purpose is to ablate, dissolve, or otherwise disrupt the clot, plaque, or other stenotic lesions which are responsible for the disease. For example, catheters constructed according to the principles of the present invention can be used to directly engage and transmit ultrasonic energy into the stenotic material in order to mechanically disrupt the material to open the associated blood vessel lumen. Such mechanical disruption can be accomplished with or without the simultaneous administration of pharmacologic and therapeutic agents. The apparatus and methods of the present invention are also useful to enhance the administration of therapeutic agents, where the therapeutic agents are primarily responsible for the disruption of the stenotic material. In such cases, the catheter may be engaged against the stenotic material, or alternatively may be maintained a short distance away from the stenotic material. The ultrasonic energy will be relied on to agitate and promote the penetration of the therapeutic agent into the stenotic material. Suitable therapeutic agents include known thrombolytic and fibrinolytic drugs, such as heparin, tissue plasminogen activator (tPA), urokinase, streptokinase, and the like. The catheters and methods of the present invention are still further useful for the treatment of vascular sites which have been previously treated by other interventional techniques, such as angioplasty, atherectomy, laser ablation, and the like. In such cases, the catheters will be used to agitate and promote the penetration of anti-thrombogenic agents into the vascular or other luminal wall to inhibit restenosis. Suitable anti-thrombogenic agents include hirudin, hirulog, heparin, tPA, urokinase, streptokinase, and the like. In addition to treatment of the vascular system, the present invention may also be used for systemic and localized delivery of drugs within other body lumens, such as the ureter, the urethra, fallopian tubes, and the like. The present invention may further be used for the systemic and localized delivery of drugs within the vascular system for treatment of non-vascular diseases, e.g., for the treatment of tumors by the localized delivery of drugs to the vasculature supporting the tumor.

The catheter of the present invention will comprise a catheter body having a proximal end and distal end. The catheter body will have dimensions and physical characteristics selected for the particular use. For vascular applications, the length of the catheter body will typically be from 50 cm to 200 cm, usually being from 75 cm to 150 cm, and the diameter will be from 1 mm to 5 mm, usually being from 2 mm to 4 mm. The diameter of the catheter body may vary over its length, and different portions of the length may be formed from different materials. In the exemplary embodiment, the catheter body will comprise a single extrusion having at least one lumen therethrough. The lumen will usually be capable of receiving a guidewire, and may also be capable of delivering therapeutic agents and/or carrying electrical wires for connection from the proximal end of the catheter body to the distal end. Alternatively, the catheter body may include separate lumens for delivering therapeutic agent(s), routing electrical wires for connection to the ultrasonic transducer, or other purposes. The catheter body may be reinforced over all or a portion of its length. Conventional reinforcement materials include wire braids, wire meshes, wire coils, and the like. When employed with a guidewire for placement within the vasculature, the catheter body may have an "over-the-wire" design or a "rapid exchange" design. In the former case, the guidewire lumen will extend substantially through the entire length of the catheter body. In the latter case, the guidewire lumen will terminate in a proximal guidewire port located relatively near the distal end of the catheter body, usually within 50 cm, more usually within 30 cm, and often within 25 cm or less. Usually, a proximal housing will be secured to the proximal end of the catheter body, where the housing includes a guidewire port, a therapeutic agent infusion port, and the like.

A resonantly vibrating assembly is secured at or near the distal end of the catheter body. The assembly will include an interface member which is resonantly vibrated at the desired ultrasonic frequency and which includes at least one interface surface for transmitting the ultrasonic vibrations to the fluid environment surrounding the distal end of the catheter. The resonantly vibrating assembly will usually be attached directly to the distal end of the catheter body but also could be disposed partially or totally within the distal end of the catheter body. Usually, the resonantly vibrating assembly will have a relatively short length, usually being below 2 cm, preferably being below 1 cm, and typically being in the range from about 0.4 cm to 1.5 cm, more usually in the range from about 0.6 cm to 1 cm. The assembly will preferably have a low profile to facilitate vascular or other intraluminal introductions, typically having a diameter below 6 mm, usually in the range from 1 mm to 5 mm, more usually in the range from 2 mm to 4 mm.

In the exemplary embodiment of the present invention, the interface surface will be forwardly disposed so that the surface may engage intraluminal obstructions as the catheter is advanced through the body lumen, such as a blood vessel. Such forwardly disposed vibrating surfaces will also be useful for projecting ultrasonic energy forwardly to agitate and promote absorption of a liquid therapeutic agent, which agent is usually delivered by the same catheter. In alternative embodiments, which are described in detail in copending application Ser. No. 08/566,739 (Attorney Docket no. 17148-000600) now pending, the interface surfaces may be laterally disposed to radiate ultrasonic energy radially outward from the catheter body.

The resonantly vibrating assembly of the present invention will further comprise a tail mass, a spring element connecting the interface member to the tail mass, and a longitudinally oscillating driver disposed between the tail mass and the interface member. The mass of the tail mass will be substantially greater than that of the interface member, typically being at least four-fold greater, and usually being at least eight-fold greater. Usually, the mass of the tail mass will be in the range from about 0.1 gm to 10 gm, more usually in the range from about 0.2 gm to 4 gm. The mass of the interface member will be in the range from 0.01 gm to 1 gm, more usually in the range from 0.03 gm to 0.1 gm. In this way, the tail mass will remain substantially stationary or immobilized while the longitudinally oscillating driver imparts longitudinal (axial) movement to the interface member. The mass of the interface member and the spring constant of the spring element will be selected so that the resonantly vibrating assembly resonates at a particular ultrasonic frequency, typically in the range from 10 kHz to 300 kHz, preferably from 20 kHz to 80 kHz. The longitudinally oscillating driver will also be selected to operate (when electronically driven) at the same ultrasonic frequency. In this way, the longitudinally oscillating driver will drive the resonantly vibrating assembly at its resonant frequency, thus enhancing the efficiency of energy transfer and increasing the amplitude of vibration (displacement) of the interface member. Preferably, the interface member will operate with a displacement (under loaded conditions) of at least about 0.5 μm, preferably in the range from 0.05 μm to 20 μm, and more preferably in the range from 0.5 μm to 2 μm.

The tail mass will usually be formed separately from the catheter body and other components of the vibratory assembly, but optionally could be formed as part of the catheter body or alternatively as an integral unit with the spring element and/or interface member. The dimensions and shape of the tail mass will usually be selected to conform to the dimensions of the catheter body, i.e., usually being a short cylinder having a diameter which is the same as or slightly smaller than that of the distal end of the catheter body.

The interface member will usually form the distal-most tip of the catheter, and will usually have a forwardly disposed convex surface which defines the interface surface. The interface surface, however, need not be convex, and could alternatively be concave, flat, irregular, or have any other geometry capable of radiating ultrasonic energy forwardly as the interface member is vibrated. Typically, the interface surface will have an area in the range from 0.5 mm$^2$ to 20 mm$^2$, preferably from 3 mm$^2$ to 12 mm$^2$.

The spring element may comprise a single rod or tube extending distally from the tail mass and attached to the proximal surface of the interface member. Usually, the single spring element will be disposed coaxially within the catheter. Alternatively, the spring element may comprise multiple rods or shafts, in which case they will usually be disposed symmetrically about the axis of the catheter.

One or more axial passages may be formed through the resonantly vibrating assembly, typically for passage of a guidewire, delivery of therapeutic agents, or the like. To provide such lumens, it will be necessary to form holes through both the tail mass and the interface member. Such holes can be aligned and joined by one or more axial components of the spring element, typically in the form of hollow tubes to provide a continuous lumen through the assembly.

The longitudinally oscillating driver can take any conventional form of ultrasonic transducer capable of converting electrical energy to mechanical ultrasonic vibrations. Exemplary transducers include piezoelectric elements, such as hollow piezoelectric cylinders, piezoelectric stacks, and the like. Suitable piezoelectric cylinders will be composed of a suitable piezoelectric material, such as a lead zirconate titinate (e.g., PZT-8), have a length in the range from 2 mm to 2 cm, an outer diameter in the range from 1 mm to 4 mm, and a wall thickness in the range from 0.1 mm to 0.5 mm. Piezoelectric stacks will comprise a plurality of ceramic disks, typically from 10 to 60 disks, having electrodes of alternate polarity disposed between the disks. Other suitable ultrasonic transducers include magnetostrictive elements, such as those described in copending application Ser. No. 08/566,740 (Attorney Docket no. 17148-000500) pending, the full disclosure of which is incorporated herein by reference.

The spring element which joins the interface member to the tail mass may comprise a single component, e.g., a single solid rod or hollow tube disposed along the longitudinal axis of the catheter or a cylindrical shell either within or external to the longitudinally oscillating driver. Alternatively, the spring element may comprise a plurality of components, such as a plurality of rods or tubes disposed symmetrically about the longitudinal axis of the catheter. The spring element may be composed of any of a wide variety of materials, most typically being a stainless steel, such as a hardened stainless steel having a Rockwell stiffness of at least about 35. The cross-sectional area of the spring element (s) shall be sufficient to provide a maximum tension of approximately 20% of the tensile strength of the material, typically about 25,000 PSI, at the time when the spring experiences its maximum deformation, i.e., the time of maximum forward displacement of the interface member. The assembly of the tail mass, interface member, and longitudinally oscillating driver is compressed by the spring mass with a static force sufficient to present continuing compressive forces at the time when the assembly shrinks to its minimum longitudinal displacement. The interface member and spring element shall have a mass and stiffness which together assure that the spring element retains compressive force on the interface member at the time of maximum reverse acceleration in order to prevent the interface member from separating from the oscillating driver. The time of maximum reverse acceleration occurs at the time of maximum forward displacement.

Referring now to FIG. 1, a catheter system 10 comprising a catheter 12 constructed in accordance with the principles of the present invention and an ultrasonic power supply 14 is illustrated. The catheter 12 includes a catheter body 16 having a distal end 18 and a proximal end 20, a proximal housing 22 having a fluid infusion port 24, and a guidewire port 26. The catheter 12 includes at least a single lumen 28 extending from the proximal end 20 to the distal end 18 and connected to both the fluid infusion port 24 and the guidewire port 26. A cable 30 extends from the proximal end 20 of the catheter body 16 (typically through the lumen 28) and includes a connector 32 which may be removably attached to the power supply 14. The power supply 14 may be selected to drive the ultrasonic transducer (described below) at about a preselected frequency. The power supply 14 will typically comprise a conventional signal generator, such as those that are commercially available from suppliers such as Hewlett-Packard, Palo Alto, Calif., and Tektronics, Portland, Oreg., and a power amplifier, such as those commercially available from suppliers such as ENI, Rochester, N.Y., and Krohn-Hite, Avon, Mass. Alternatively, the power supply may comprise custom signal generator and power amplifier circuits with tracking circuits to keep the driving frequency at the resonant frequency of the ultrasonic driver in the catheter tip as this resonant frequency drifts due to thermally induced material variations.

Figure 2:
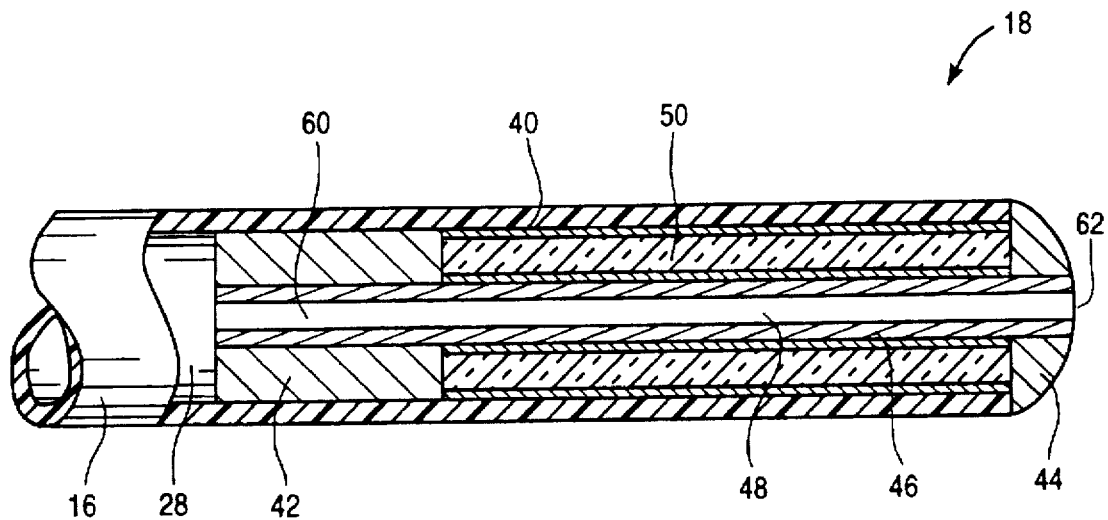
FIG. 2 is a detailed view of the distal end of the catheter of FIG. 1, shown in partial section.
Figure 3:
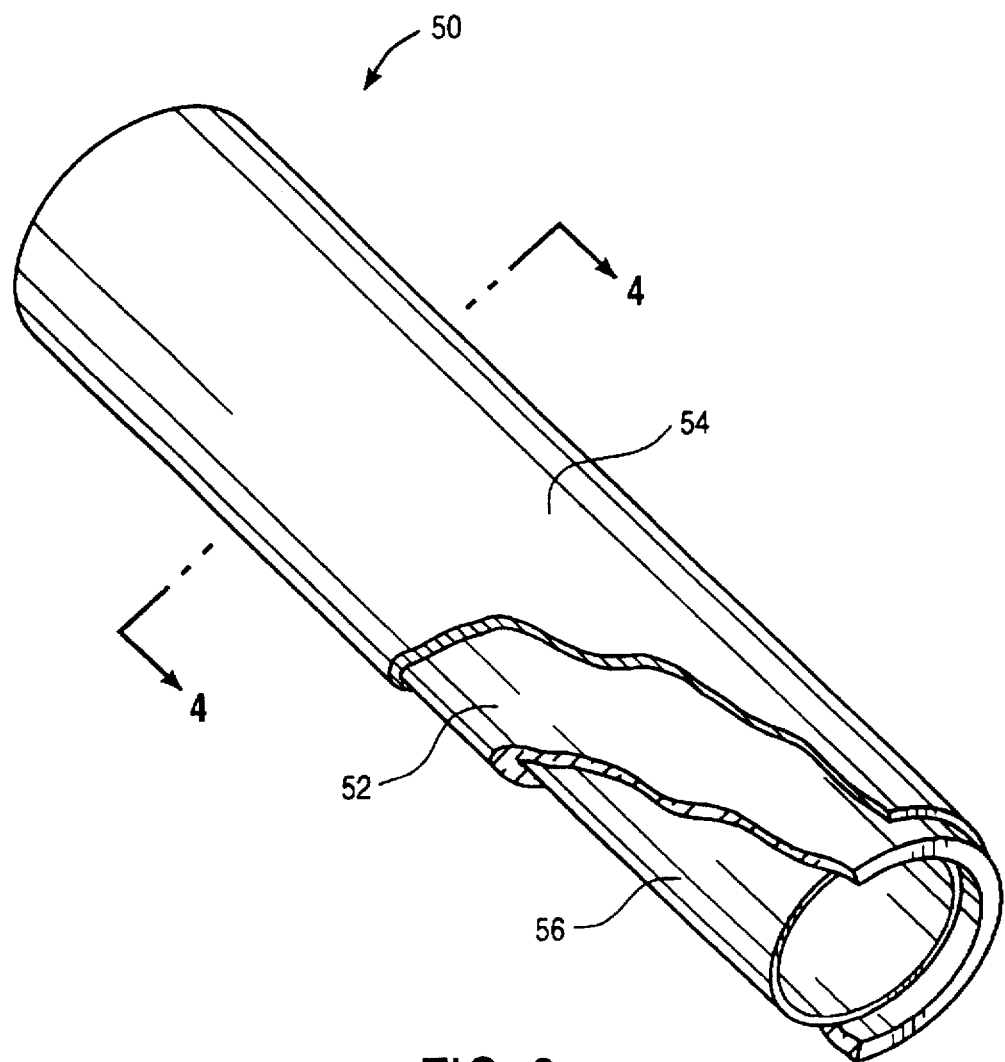
FIG. 3 is a perspective view of the tubular piezoelectric transducer which is incorporated in the catheter of FIG. 1.
Figure 4:
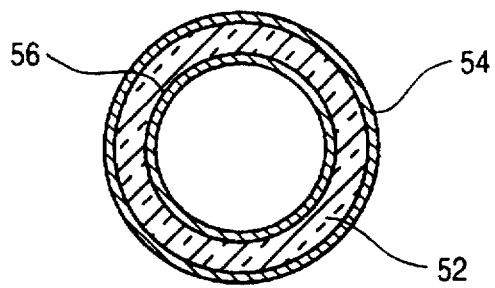
FIG. 4 is a cross-sectional view taken along line 4—4 of FIG. 3.

Referring now to FIGS. 2–4, a resonantly vibrating assembly 40 is mounted within the distal end of the catheter body 16. The resonantly vibrating assembly 40 comprises a tail mass 42, an interface member 44, and a spring element 46 in the form of a tube having a lumen 48 therethrough. The tubular spring element 46 is connected at its distal end to the interface member 44 and at its proximal end to the tail mass 42. Attachment of these components can be achieved in conventional ways, such as threaded attachment joints, the use of adhesives such as epoxy, solder joints, welded joints, and the like.

Figure 5:
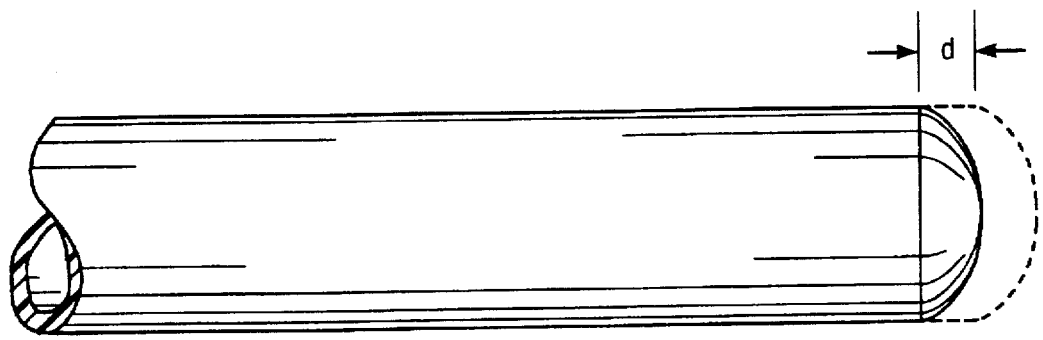
FIG. 5 is a detailed view of the distal end of the catheter of FIG. 1, with the extent of longitudinal oscillation being shown in broken line.

A longitudinally oscillating driver 50 is mounted between the tail mass 42 and the interface member 44. The driver 50 is a tubular piezoelectric transducer, as best illustrated in FIGS. 3 and 4. The tubular transducer includes a piezoelectric tube 52 formed from a suitable material, as described above, sandwiched between an outer electrode 54 and inner electrode 56. Often, a small annular gap will be left between the driver 50 and the inner wall of the catheter body 16 and/or the outer wall of the spring element 46, although the gap is not shown in FIG. 2. Application of a suitable driving voltage to the electrodes 54 and 56 will cause the tubular transducer to oscillate both longitudinally and radially. A suitable driving voltage will be from 10 V to 200 V. The resulting axial displacement is best observed in FIG. 5, where displacements in the range from 0.05 µm to 20 µm, usually from 0.5 µm to 2 µm, may be achieved.

A lumen 60 is formed through the tail mass and a second lumen 62 is formed through the interface member. The lumens 60 and 62 are aligned with the lumen 48 through the driver 50. In this way, a continuous lumen is provided from the lumen 28 of the catheter body through the distal tip of the catheter. This lumen is suitable for introducing the catheter over the guidewire and/or delivering therapeutic agents through the catheter and releasing said agents from the distal tip.

Figure 6:
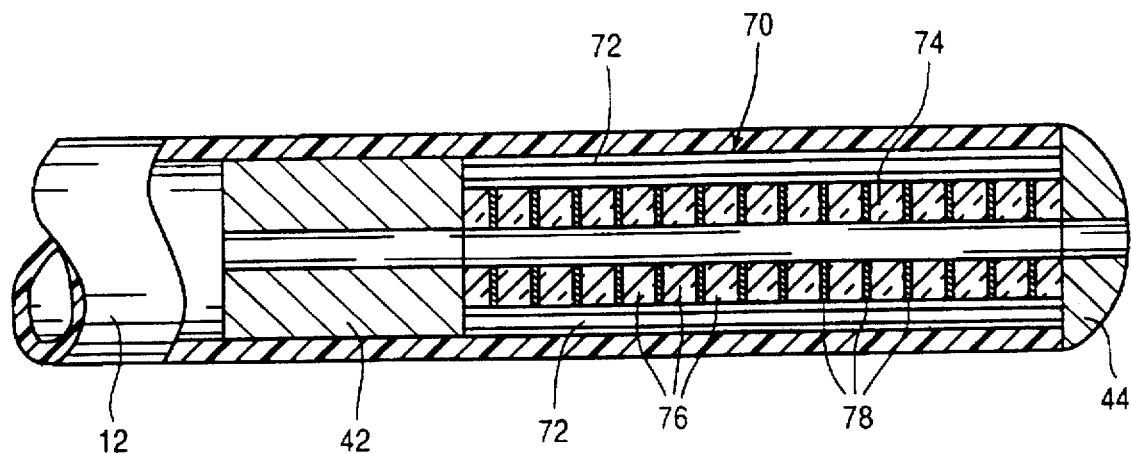
FIG. 6 is an alternative detailed view of the distal end of the catheter of FIG. 1, shown in partial section.
Figure 7:
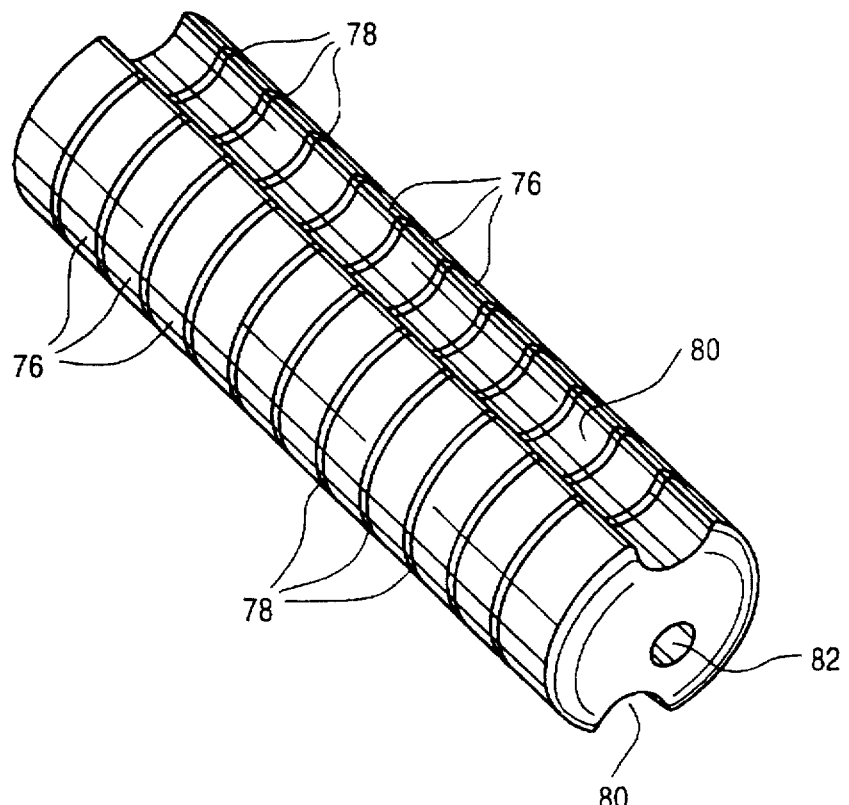
FIG. 7 is a perspective view of the piezoelectric stack ultrasonic transducer incorporated in the design of FIG. 6.

An alternative resonantly vibrating assembly 70 is illustrated in FIGS. 6 and 7. Catheter body 12, tail mass 42, and interface member 44 may all be identical to those described in connection with FIGS. 1–5. The spring element, however, comprises a pair of radially offset shafts 72 which are disposed symmetrically about the axis of the catheter. A longitudinally oscillating driver 74 comprises a stack of piezoelectric disks 76 which are sandwiched between electrode plates 78, as best illustrated in FIG. 7. The electrodes 78 will be connected to positive and negative terminals of the power supply 14 in order to induce longitudinal vibrations in the piezoelectric stack. The stack may be machined to include opposed channels 80 to accommodate the rods 72 as well as a central lumen 82 for accommodating a guidewire and/or the delivery of fluids.

Figure 8:
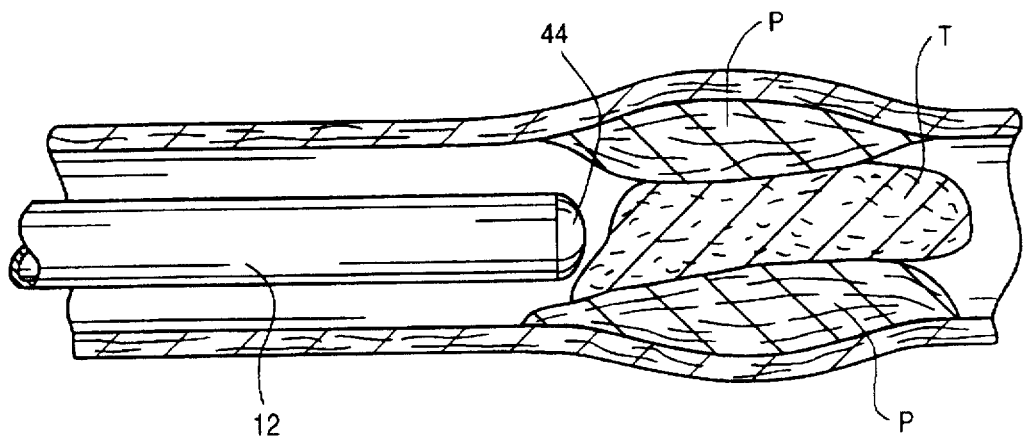
FIG. 8 illustrates use of the catheter of FIG. 1 in a first protocol for ultrasonically ablating clot by direct engagement with the clot.

Referring now to FIG. 8, use of the catheter 12 for directly engaging a region of thrombus T in a diseased blood vessel BV having a region of plaque P is illustrated. The forwardly disposed interface surface of interface member 44 is advanced through the lumen of the blood vessel in a conventional manner until it engages the thrombus T. The resonantly vibrating assembly will then be activated to cause ultrasonic vibration of the interface member 44. The interface surface of the interface member, in turn, will transmit the ultrasonic vibrations directly into the thrombus T, resulting in mechanical disruption of the thrombus and clot. Optionally, a thrombolytic or fibrinolytic agent may be delivered through the catheter 12 and released into a region proximal to the thrombus T, either before, during or after the mechanical disruption. Preferably, the ultrasonic energy will be transmitted while the treatment agent is being released to enhance penetration of the agent into the thrombus T.

Figure 9:
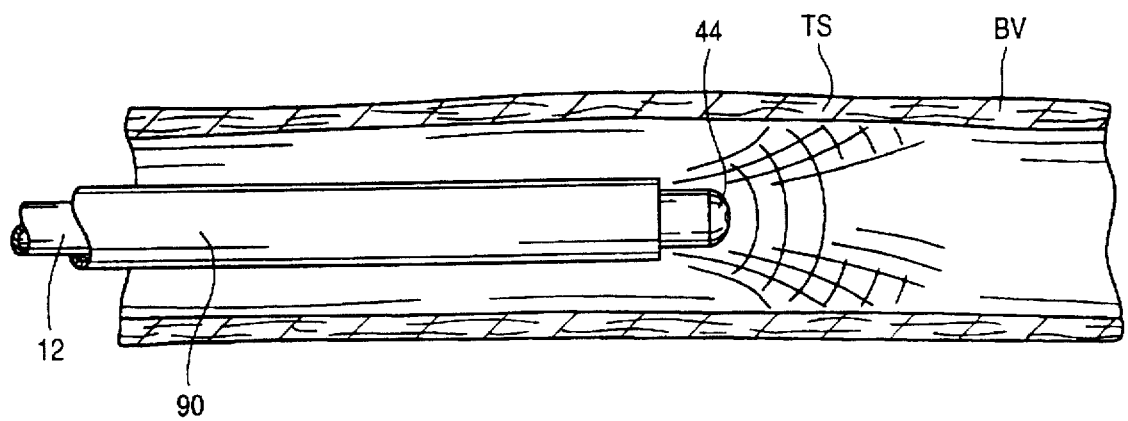
FIG. 9 illustrates use of the catheter of FIG. 1 in a second protocol for ultrasonically enhancing the activity of a therapeutic agent released from the distal end of the catheter.

An alternative treatment method is illustrated in FIG. 9. There, a sleeve catheter 90 is disposed over the catheter 12 of the present invention. An anti-thrombogenic treatment agent is delivered through the sleeve catheter 90 to a target site TS within a blood vessel BV. The interface member 44 is ultrasonically vibrated, as described previously. The ultrasonic vibration will enhance penetration of the agent into the wall of the blood vessel BV. This method would be equally suitable for delivering drugs into other body lumens. Use of the sleeve catheter 90 for delivering drugs is illustrated as an alternative to delivering the drugs through the lumen of the catheter 12 itself. It will be appreciated that the sleeve catheter 90 could have been used in the method of FIG. 8. Conversely, the lumen of catheter 12 could have been used to deliver the anti-thrombogenic agent in the method of FIG. 9.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A catheter comprising:
   a catheter body having a proximal end and a distal end;
   a tail mass attached to the catheter body;
   a longitudinally oscillating driver engaging and extending distally from the tail mass;
   an interface member engaging a distally forward surface of the oscillating driver, wherein the mass of the interface member is much less than that of the tail mass; and
   a spring element connecting the tail mass to the interface member, wherein the spring element has a spring force which is selected to permit resonant driving by the longitudinally oscillating driver.

2. A catheter as in claim 1, wherein the longitudinally oscillating driver comprises a longitudinally oscillating member selected from the group consisting of piezoelectric elements and magnetostrictive elements.

3. A catheter as in claim 2, wherein the longitudinally oscillating member comprises a hollow piezoelectric cylinder having an inner cylindrical electrode and an outer cylindrical electrode.

4. A catheter as in claim 3, wherein piezoelectric cylinder has dimensions and is composed of a material which provide oscillation at a frequency in the range from 10 kHz to 300 kHz.

5. A catheter as in claim 4, wherein the piezoelectric cylinder is composed of a lead zirconate titinate, has a length in the range from 2 mm to 2 cm, an outer diameter in the range from 1 mm to 4 mm, and a wall thickness in the range from 0.1 mm to 0.5 mm.

6. A catheter as in claim 2, wherein the longitudinally oscillating member comprises a plurality of ceramic disks having electrodes therebetween.

7. A catheter as in claim 1, wherein the tail mass has a mass which is at least four times the mass of the interface member.

8. A catheter as in claim 7, wherein the tail mass has a mass in the range from 0.1 gm to 10 gm and the interface member has a mass in the range from 0.01 gm to 1 gm.

9. A catheter as in claim 1, wherein the spring element comprises at least one rod secured at a proximal end to the tail mass and at a distal end to the interface member.

10. A catheter as in claim 9, wherein the spring element consists of a single rod disposed coaxially within the catheter.

11. A catheter as in claim 9, wherein the spring element comprises at least two parallel rod members disposed symmetrically about the axis of the catheter body.

12. A catheter as in claim 1, wherein the interface member includes a distally disposed interface surface which forwardly transmits longitudinal oscillations into the environment surrounding the distal end of the catheter.

13. A catheter as in claim 12, wherein the interface surface has a generally convex shape.

14. A catheter as in claim 1, wherein the catheter body has at least one lumen for delivering a therapeutic agent therethrough.

15. An improved ultrasonic catheter of the type comprising a catheter body having an ultrasonic driver at a distal end thereof, wherein the improvement comprises an ultrasonic driver comprising:
   a tail mass secured to the distal end of the catheter body;
   an interface member distally spaced-apart from the tail mass;
   a spring element connecting the interface member to the tail mass;
   an ultrasonic driver disposed between the interface member and the tail mass, wherein said driver oscillates at or near a resonant frequency characteristic of the interface member, the spring element, and the ultrasonic driver.

16. A catheter as in claim 15, wherein the ultrasonic driver comprises a hollow piezoelectric cylinder having an inner cylindrical electrode and an outer cylindrical electrode.

17. A catheter as in claim 16, wherein the piezoelectric cylinder has dimensions and is composed of a material which provide oscillation at a frequency in the range from 10 kHz to 300 kHz.

18. A catheter as in claim 17, wherein the piezoelectric cylinder is composed of a lead zirconate titinate, has a length in the range from 2 mm to 2 cm, an outer diameter in the range from 1 mm to 4 mm, and a wall thickness in the range from 0.1 mm to 0.5 mm.

19. A catheter as in claim 15, wherein the ultrasonic driver comprises a plurality of ceramic disks having electrodes therebetween.

20. A catheter as in claim 15, wherein the tail mass has a mass which is at least four times the mass of the interface member.

21. A catheter as in claim 20, wherein the tail mass has a mass in the range from 0.1 gm to 10 gm and the interface member has a mass in the range from 0.01 gm to 1 gm.

22. A catheter as in claim 15, wherein the spring element comprises at least one rod secured at a proximal end to the tail mass and at a distal end to the interface member.

23. A catheter as in claim 22, wherein the spring element consists of a single rod disposed coaxially within the catheter.

24. A catheter as in claim 22, wherein the spring element comprises at least two parallel rod members disposed symmetrically about the axis of the catheter body.

25. A catheter as in claim 15, wherein the interface member includes a distally disposed interface surface which forwardly transmits longitudinal oscillations into the environment surrounding the distal end of the catheter.

26. A catheter as in claim 25, wherein the interface surface has a generally convex shape.

27. A catheter as in claim 15, wherein the catheter body has at least one lumen for delivering a therapeutic agent therethrough.

28. A method for treating intraluminal lesions, said method comprising:

providing a catheter having an assembly comprising an interface member connected to a tail mass by a spring element disposed at its distal end, wherein the assembly has a resonant frequency;

advancing a forwardly disposed surface of the interface member to a region near the intraluminal lesion;

driving the interface member relative to the tail mass at the resonant frequency, wherein ultrasonic energy is amplified and radiated into the region.

29. A method as in claim 28, wherein the intraluminal lesion contains a vascular stenosis.

30. A method as in claim 29, wherein the interface member surface is engaged against a vascular obstruction.

31. A method as in claim 28, wherein the interface member is driven at a frequency in the range from about 10 kHz to 300 kHz.

32. A method as in claim 31, wherein the interface member is driven with a longitudinal amplitude in the range from 0.05 µm to 20 µm.

33. A method as in claim 28, wherein the forwardly disposed surface has an area in the range from 0.5 mm$^2$ to 20 mm$^2$.

34. A method as in claim 28, further comprising delivering a therapeutic agent through the catheter to the intraluminal lesion.

35. A method as in claim 34, wherein the therapeutic agent is delivered while ultrasonic energy is being radiated into the region.

36. A method as in claim 35, wherein the therapeutic agent is a fibrinolytic agent delivered to a vascular stenosis to treat clot.

37. A method as in claim 35, wherein the therapeutic agent is delivered to a previously treated vascular site to inhibit restenosis.

* * * * *